United States Patent [19]
LaRue et al.

[11] Patent Number: 5,374,826
[45] Date of Patent: Dec. 20, 1994

[54] HYBRID PHOTOMULTIPLIER TUBE WITH HIGH SENSITIVITY

[75] Inventors: Ross A. LaRue, Milpitas; Kenneth A. Costello, Union City; Verle W. Aebi, Menlo Park, all of Calif.

[73] Assignee: Intevac, Inc., Santa Clara, Calif.

[21] Appl. No.: 91,764

[22] Filed: Jul. 14, 1993

Related U.S. Application Data

[63] Continuation-in-part of Ser. No. 992,430, Dec. 17, 1992, Pat. No. 5,326,978.

[51] Int. Cl.$^5$ ............................................. H01J 31/30
[52] U.S. Cl. ................................. 250/397; 250/207; 313/532
[58] Field of Search ................. 250/397, 207; 313/532

[56] References Cited

U.S. PATENT DOCUMENTS

| | | | |
|---|---|---|---|
| 3,345,537 | 10/1967 | Spencer | 315/85 |
| 3,391,295 | 7/1968 | Clayton | 250/207 |
| 3,805,058 | 4/1974 | Glaenzer | 250/207 |
| 3,885,178 | 5/1975 | Goehner | 313/1 |

FOREIGN PATENT DOCUMENTS

| | | |
|---|---|---|
| 2334194 | 7/1977 | European Pat. Off. |
| 9009681 | 8/1990 | European Pat. Off. |

OTHER PUBLICATIONS

L. K. vanGeest et al, "Hybrid Phototube with Si Target", SPIE, vol. 1449, Elec. Image Tubes & Image Inten. II, 1991, pp. 121–134.
K. C. Schmidt et al, "Con. Channel Elect. Mult. Op. in the Pulse Saturated Mode", IEEE Trans. Nucl. Sci., Jun. 1966, pp. 100–111.
J. P. Edgecumbe et al, "A GaAsP Photocathode with 40% QE at 515nm", SPIE, vol. 1655, Elect. Tubes and Image Inten., Feb. 1992.
K. A. Costello et al, "Transferred Elect. Photocathode with Greater Than 5% Quan. Eff. Beyond One Micron", SPIE, vol. 1449, Elect. Tubes and Image Intensifiers II, 1991.

*Primary Examiner*—Paul M. Dzierzynski
*Assistant Examiner*—Kiet T. Nguyen
*Attorney, Agent, or Firm*—Stanley Z. Cole

[57] ABSTRACT

A focused electron/bombarded (FEB) ion detector comprising an MCP, focusing means, and a collection anode disposed in a detector body. The collector anode includes a diode for receiving the focused output electron beam from the MCP. The gain between the input ion current to the MCP and the detector output signal from the diode is on the order of 1-100 million, depending on the device configuration and applied biasing voltages. A hybrid photomultiplier tube includes a photocathode, a photodiode for collecting and multiplying electrons emitted by the photocathode and providing an output signal and electrodes for focusing the electrons on the photodiode. A vacuum envelope encloses a vacuum region between photocathode and the detector. A conductor disposed on or adjacent to a sidewall of the vacuum envelope reduces the effect of electrical charges on the inside wall of the vacuum envelope on the trajectories of the electrons.

26 Claims, 7 Drawing Sheets

HYBRID PHOTOMULTIPLIER TUBE WITH HIGH SENSITIVITY

CROSS REFERENCE TO RELATED APPLICATION

This application is a continuation in part of Ser. No. 07/992,430, filed Dec. 17, 1992, now U.S. Pat. No. 5,326,978.

FIELD OF THE INVENTION

This invention relates to photomultiplier tubes and, more particularly, to hybrid photomultiplier tubes which have a conductor on or adjacent to the vacuum envelope to reduce the effect of electrical charges on the wall of the vacuum envelope on electron trajectories within the tube.

BACKGROUND OF THE INVENTION

Conventional photomultiplier tubes include a vacuum envelope containing a photocathode, several dynodes and an electron collector. Light entering the tube through a window and incident on the photocathode causes electrons to be emitted by the photocathode. The electrons impinge on the successive dynodes, causing electron multiplication by secondary emission. After impingement on the last dynode, the electrons are collected and delivered on an output lead of the tube to provide an output signal which is representative of the input light.

A hybrid photomultiplier tube includes a photocathode, electron focusing electrodes and an electron bombarded photodiode anode. Electrons emitted by the photocathode are focused onto the photodiode. The electrons penetrate into the photodiode material and create electrode-hole pairs, causing a multiplication effect. Gain is produced by the photodiode rather than the dynodes, as in the conventional photomultiplier tube.

A hybrid photomultiplier is disclosed by L. K. van Geest et al in "Hybrid Phototube With Si Target", SPIE, Vol. 1449, *Electron Image Tubes and Image Intensifiers, II*, 1991, pages 121-134. A photomultiplier tube using both dynodes and an impact ionization diode for electron multiplication is disclosed in U.S. Pat. No. 3,885,178 issued May 20, 1975 to Goehner.

A bias voltage on the order of 10 kilovolts is typically applied between the anode and cathode of a hybrid photomultiplier tube. The electrons are accelerated by the applied field and bombard the photodiode anode, which results in multiplication gain. However, depending on the photodiode material, 20-30% of the electrons backscatter off the diode surface at varying angles. Some of the electrons strike the inside surface of the tube wall, causing charging of the tube wall. The charges modify the potential inside the tube, causing a defocusing of the electron beam and operational instability. In addition, for a sufficiently large acceleration voltage, x-rays may be generated at the diode surface due to electron deceleration. The x-rays can strike the inside surface of the tube wall, resulting in ionization or positive charging of the surface. Again, the net result is electron defocusing and operational instability. A curved channel electron multiplier, wherein part of the outer surface was coated with a silver film to determine the effect of distributed capacitance on various parameters, is disclosed by K. C. Schmidt et al in "Continuous Channel Electron Multiplier Operated in the Pulse Saturated Mode", *IEEE Trans. Nucl. Sci.*, June 1966, p. 100-111.

One prior art approach to the wall charging problem in photomultiplier tubes involves a partially conductive coating, such as green or black chrome oxide, on the inside surface of the tube wall. However, the coating must be highly resistive to prevent short circuiting of the tube electrodes. Thus, the coating is not particularly effective in reducing the effect of wall charging. Furthermore, the tube life may be reduced by outgassing from suck coatings into the vacuum envelope.

SUMMARY OF THE INVENTION

A photomultiplier tube in accordance with the present invention comprises a photocathode for emitting electrons in response to incident photons, a detector for collecting and multiplying the electrons emitted by the photocathode and providing an output signal representative of the incident photons, electron optical means for controlling the trajectories of the electrons between the photocathode and the detector, means for accelerating the electrons between the photocathode and the detector, a vacuum envelope enclosing a vacuum region between the photocathode and the detector, and a conductor disposed on or adjacent to at least a portion of the vacuum envelope for reducing the effect of electrical charges on the vacuum envelope on the trajectories of the electrons. The electron optical means typically comprises first and second focusing electrodes.

The conductor is preferably disposed on an outside surface of the vacuum envelope as a conductive coating or conductive paint. In a preferred embodiment, the conductor comprises a first conductive coating formed on the vacuum envelope and electrically connected to the photocathode and a second conductive coating formed on the vacuum envelope and electrically connected to the first focusing electrode. The first and second conductive coatings are spaced apart by a gap.

The photocathode is typically located on an inside surface of a window in the vacuum envelope. The photocathode preferably comprises a group III-V semiconductor material, such as gallium arsenide, gallium arsenide phosphide, indium phosphide or indium phosphide/indium gallium arsenide.

The vacuum envelope preferably includes a coaxial feedthrough for coupling the output signal externally of the vacuum envelope. The photodiode preferably comprises an avalanche photodiode mounted on a center conductor of the coaxial feedthrough.

According to another aspect of the invention, there is provided an improved vacuum tube of the type including a vacuum envelope, a charged particle source within the vacuum envelope for emitting charged particles, and optics for controlling the trajectories of the charged particles within the vacuum envelope. The improvement comprises a conductor disposed on or adjacent to at least a portion of the vacuum envelope for reducing the effect of electrical charges onethe vacuum envelope on the trajectories of the charged particles.

BRIEF DESCRIPTION OF THE DRAWINGS

For a better understanding of the present invention, reference is made to the accompanying drawings, which are incorporated herein by reference and in which.

DETAILED DESCRIPTION OF THE PREFERRED EMBODIMENTS

Figure 1:
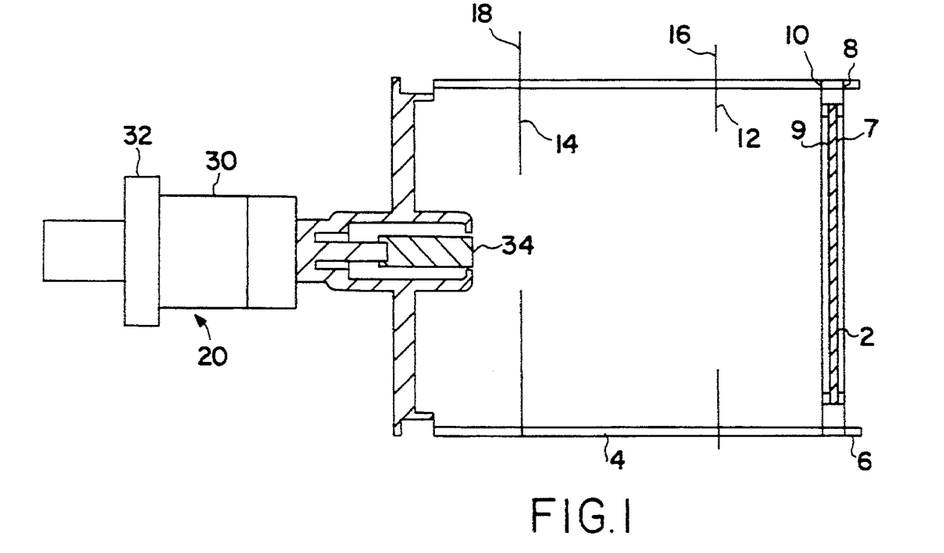
FIG. 1 is a cross-sectional view of an FEB ion detector.
Figure 2:
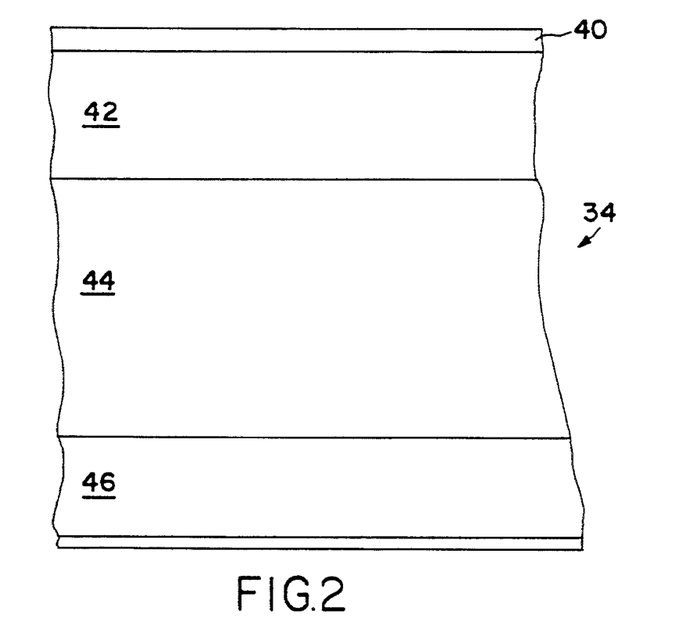
FIG. 2 is a detailed view of the diode element of the FEB ion detector.

An FEB ion detector is shown in FIGS. 1 and 2. A standard microchannel plate (MCP) 2 is mounted at one end of a cylindrical detector body 4. In the embodiment shown in FIG. 1, detector body 4 is comprised of a series of ceramic rings stacked to give the appropriate dimensions. Alternatively, the detector body could be formed as a specially designed cylinder or in any other shape dictated by the application. MCP 2 is held in place by a retainer ring 6. Conductors 8 and 10 extend from the MCP input electrode 7 and MCP output electrode 9, respectively, to attach the ion detector to a suitable power source (not shown).

Figure 3:
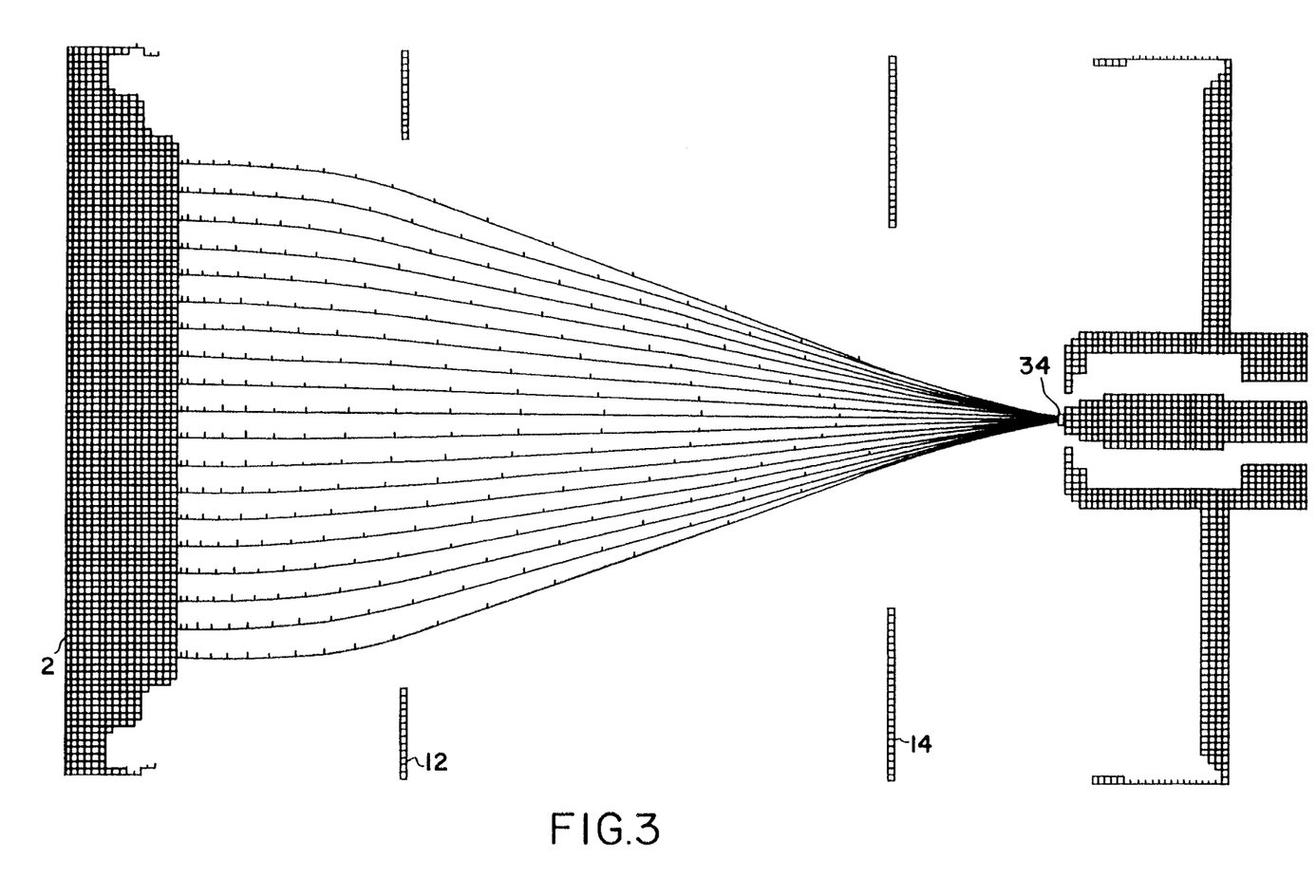
FIG. 3 is a schematic drawing showing the operation of the FEB ion detector.

Two electron focusing rings 12 and 14 are disposed in detector body 4. In the embodiment shown in FIG. 1, rings 12 and 14 are mounted between pairs of the ceramic rings comprising detector body 4. Other means of attaching the focusing rings may be used without departing from the invention. Rings 12 and 14 connect to an external power source (not shown) via suitable conductors 16 and 18, respectively. The purpose of focusing rings 12 and 14 is to concentrate and direct the output of the MCP onto the collection anode, as shown schematically in FIG. 3.

A collection anode 20 is disposed at the far end of detector body 4. Anode 20 comprises a broadband microwave connector 30, a step-tapered coaxial transmission line section 32, and a solid state diode 34 terminating the transmission line. In a preferred embodiment, diode 34 is an AlGaAs/GaAs pin diode optimized for electron bombardment current gain. As shown in more detail in FIG. 2, the preferred embodiment of diode 34 comprises three separate layers 40, 42 and 44 formed on an n+GaAs substrate 46. The top layer 40 is doped to be a p-type Al$_{30}$Ga$_{70}$As layer approximately 250 Angstoms thick. Layer 40 provides a potential barrier near the surface of the diode to keep generated electron minority carriers from recombining at the surface. The composition of layer 40 is also chosen for stability and for its resistance to oxidation during processing in air. Layer 42 is doped to be p-type GaAs approximately 0.25 microns thick.

Layer 44 is undoped GaAs and is approximately 6 microns thick. The thickness of layer 44 is chosen to optimize the response time of the diode according to the following principles:

The transit time $T_{transit}$ of an electron across an undoped layer of thickness w is $$T_{transit} = w/V_{sat}$$

where $V_{sat}$ is $1 \times 10^7$ cm/sec. The RC time constant $T_{RC}$ of the loaded diode is $$T_{RC} = E\ (\pi r^2/w)\ R_L$$

where r is the radius of the diode and $R_L$ is the diode load (50$\phi$, for example). The time response of the loaded diode is minimized when $T_{transit} = T_{RC}$ or, $$w/V_{sat} = E\ (\pi r^2/w)\ R_L$$

The optimum w or undoped thickness is therefore $$w = \text{Square Root of } (E\ \pi r^2\ V_{sat} R_L)$$

The optimum time response is therefore $$T_{opt} = \text{Square Root of } (E\pi r^2\ R_L/V_{sat})$$

Since $T_{opt}$ is proportional to diode radius, the time response of an FEB detector using such a diode is greatly improved over detectors which do not focus.

The following is an example of the design and operating parameters of an FEB ion detector according to a preferred embodiment. The MCP of this example has a plate diameter of 19 mm and a channel diameter of 10 microns. An outside power source applies a potential of approximately 1000 volts across the MCP's input and output electrodes 7 and 9. In addition, the power source applies a potential of approximately 30 volts between MCP output electrode 9 and the first focusing ring 12 and a potential of approximately 400 volts between MCP output electrode 9 and the second focusing ring 14. Collection anode 20 is grounded, making the voltage drop between diode 34 and the MCP output approximately 10,000 volts.

In operation, charged particles (such as positive ions) strike the MCP channel walls and create electrons. The electrons are accelerated by the voltage across the MCP and strike the channel walls to generate additional electrons. This multiplication of electrons results in a flux of electrons at the MCP output end with a net gain of electron charge per incident charged particle. The generated electrons are then accelerated and focused by the focusing rings 12 and 14. The focusing rings of the FEB ion detector reduce the diameter of the MCP output from 18 mm at the output electrode to a 0.25 mm diameter beam at collection anode 20 (as shown schematically in FIG. 3), and the bias applied to the MCP and focusing rings raises the average energy of the electrons striking diode 34 to 10,000 eV. The gain of the FEB ion detector may be adjusted by changing the bias voltage of the MCP (i.e., by changing the voltage between the MCP input and output electrodes) and by changing the overall bias between the MCP, the focusing rings and the collection anode. For an MCP bias voltage of 1000 volts and overall bias voltage of 10,000 volts as described in this example, the FEB ion detector gain is on the order of 90 million.

Figure 4A:
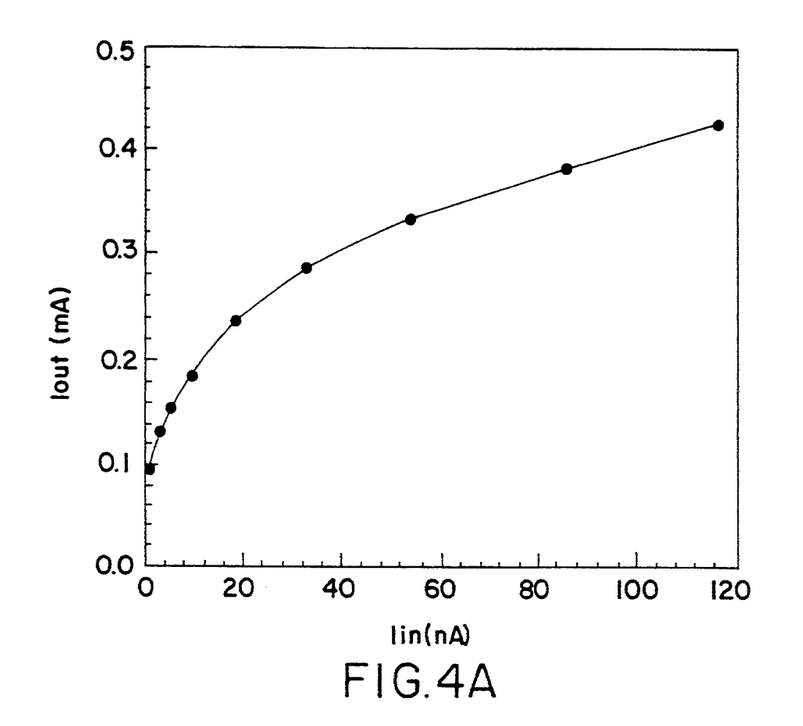
FIG. 4A is an actual measured transfer curve of output current vs. input current for the FEB ion detector.
Figure 4B:
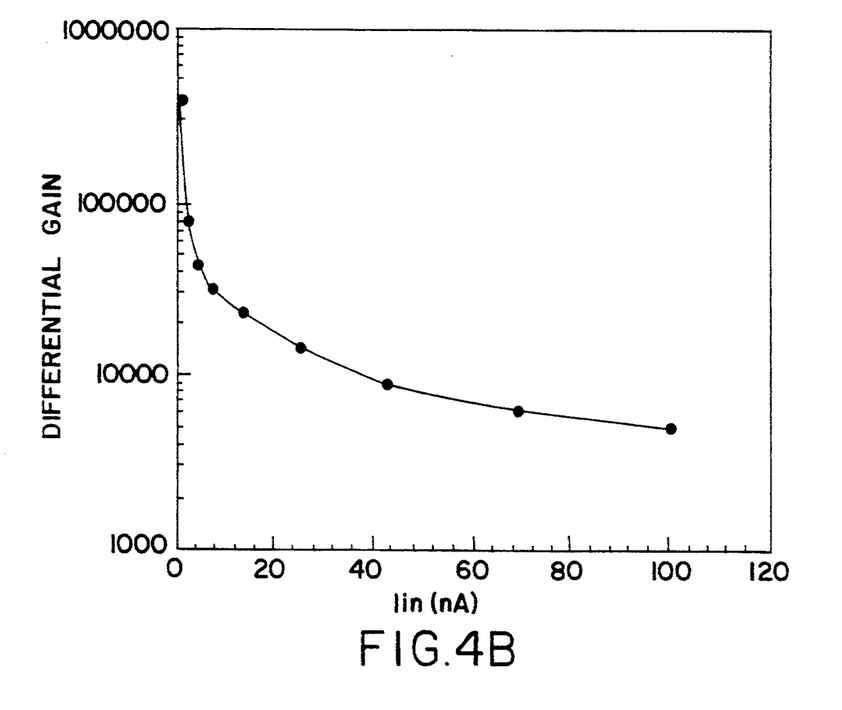
FIG. 4B is a curve illustrating the differential gain vs. input current calculated from FIG. 4A.

FIG. 4A shows the measured transfer curve (diode output current versus input current), and 4B shows the differential gain of a prototype FEB ion detector. Here the detector is used to detect input electron current. The gain is approaching one million at one nanoamp input current.

The FEB ion detector improves upon current ion detectors such as channeltrons and MCP stacks by improving the device's bandwidth and dynamic range due to the pin diode's ability to handle relatively high instantaneous currents while still delivering a linear response. The FEB detector also has a lower capacitance, and therefore a faster recovery time, than prior art detectors.

The FEB detector has a longer useful life than current channeltron or MCP stack ion detectors. The high gain at which channeltrons and MCP stacks need to be operated increases the electron bombardment rate on the devices' outputs. The higher bombardment rate deteriorates the interior surface of the channels, causing them to be less emissive. However, this form of deterioration is avoided with the FEB ion detector of this invention because the MCP is operated at a lower gain.

The FEB detector does not have the same stringent vacuum requirements that MCP stacks and channeltrons have. The high gain of current MCP stacks and channeltrons creates high electron densities within the channels. Collisions between the electrons and any gas molecules present in the channels can create positive ions. As the positive ions move toward the input end of the channels under the influence of the bias voltage, they strike the channel walls and create "noise" electrons. Higher bias voltages create more ions and increase this noise effect. Since the FEB detector of this invention can be operated at lower bias voltages than current channeltrons and MCP stacks, fewer ions are created in the channels at given gas molecule concentrations. The FEB detector can therefore be used under less stringent vacuum conditions than current detectors with ion noise effect kept to a minimum.

The example described above is but one of many possible configurations other configurations of FEB detectors are within the scope of this invention. In one alternative embodiment, for example, a silicon or GaAs avalanche photodiode may be substituted for the solid state diode described above to give added gain. In addition, the detector could employ more than one MCP in a serial (stacked) arrangement to improve the gain of the detector.

In another alternative embodiment, the focusing rings may be modified and more focusing rings may be added to optimize the focusing for the application. In addition, the single diode 34 may be replaced with an array of diodes to provide positional information.

The dimension and properties of the FEB detector should be selected to meet the application. For example, the MCP may be designed with a larger diameter to increase the detector input area. The communication between the diode and the device monitor-may be optimized by impedance matching the diode and the coaxial transmission line in a manner known in the art. Impedance matching helps keep The response of the detector flat over the dynamic range of frequencies.

While the FEB ion detector has been described with reference to the detection of ions, the FEB detector may be used to detect any particle that generates electrons when striking the channel walls of an MCP, such as an X-ray, a photon or an energetic neutral particle. In addition, although the FEB detector has been described in terms of ordinary MCPs, the walls of such MCPs may also be doped or coated to enhance the electron generation effect in a manner known in the art, for use in this invention.

Figure 5:
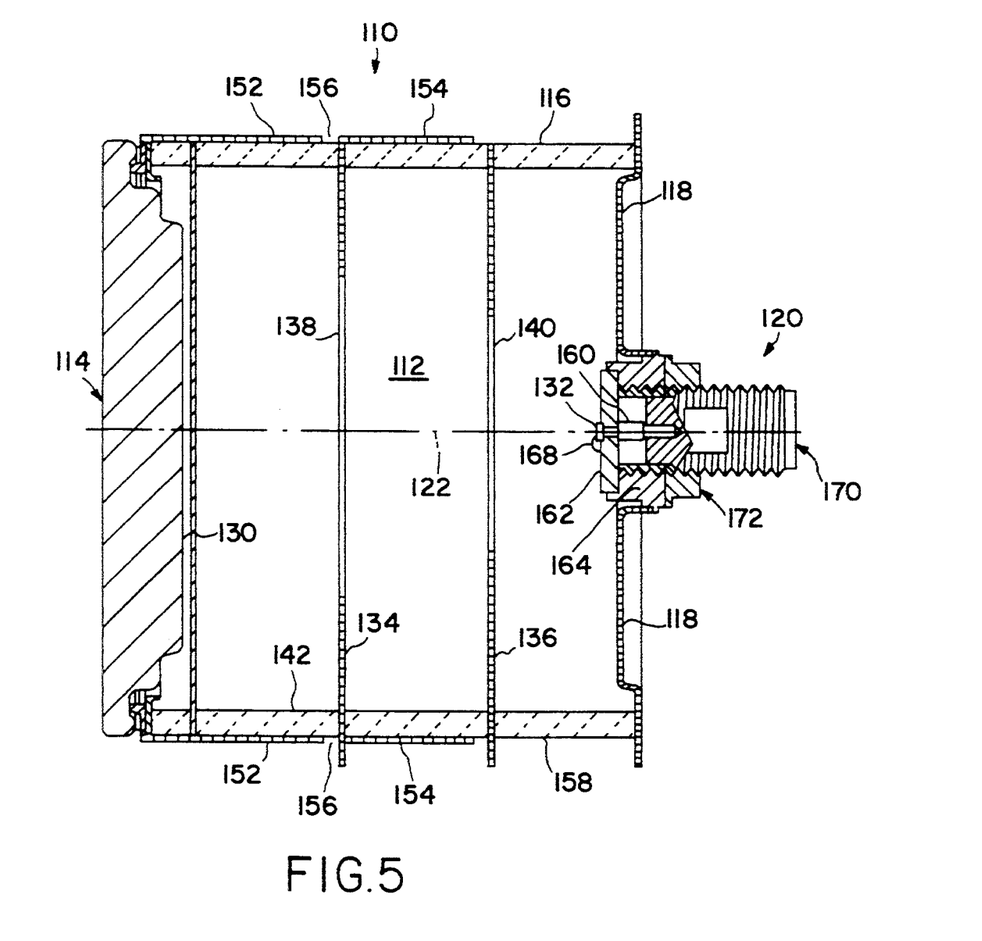
FIG. 5 is a cross-sectional view of a hybrid photomultiplier tube in accordance with the present invention.

A preferred embodiment of a hybrid photomultiplier tube is shown in FIG. 5. Equipotential electric field lines and electron trajectories of the hybrid photomultiplier tube are shown in the schematic diagram of FIG. 6. A vacuum envelope 110, or housing, encloses a vacuum region 112, typically having a pressure on the order of $10^{-10}$ torr. The vacuum envelope 110 includes a window 114, a sidewall 116, an electrode 118 and a connector assembly 120. The sidewall 116 typically comprises several ceramic rings. The vacuum envelope 110 typically has circular symmetry about a central axis 122 such that the sidewall 116 is cylindrical. However, the vacuum envelope 110 may have other physical configurations.

A photocathode 130 is located on the inside surface of window 114. The photocathode 130 is preferably a group III-V semiconductor material, such as gallium arsenide, gallium arsenide phosphide, indium phosphide or indium phosphide/indium gallium arsenide. A suitable gallium arsenide phosphide photocathode is disclosed by J. P. Edgecumbe et al in "A GaAsP Photocathode With 40% QE at 515 nm", SPIE Vol. 1655, *Electron Tubes and Image Intensifiers*, February 1992. A suitable gallium arsenide photocathode is disclosed by K. A. Costello et al in "Imaging GaAs Vacuum Photodiode with 40% Quantum Efficiency at 530 nm", SPIE Vol. 1243, *Electron Image Tubes and Image Intensifiers*, 1990. Another suitable photocathode is disclosed by K. Costello et al in "Transferred Electron Photocathode with Greater Than 5% Quantum Efficiency Beyond One Micron", SPIE Vol. 1449, *Electron Tubes and Image Intensifiers II*, 1991. Typically, a wafer including layers of epitaxially grown, suitable photocathode material is bonded to window 114, and the wafer substrate is etched away in the case of GaAs or GaAsP photocathodes. In the case of a transferred electron photocathode, the substrate may be left intact or removed. The photocathode 130 emits electrons in response to incident light received through window 114.

The electrons emitted by photocathode 130 are focused on a photodiode 132 by electrodes 134 and 136 sealed within the vacuum envelope 110. The electrodes 134 and 136 have central apertures 138 and 140, respectively, for passage of the electrons to photodiode 132. The placement and dimensions of the electrodes 134 and 136 are selected to focus electrons emitted by photocathode on photodiode 132. Additional focusing electrodes can be used, if desired.

Photocathode 130 is typically biased at about $-10$ Kv. At this photocathode voltage, electrode 134 is typically biased at $-9878$ volts, and electrode 136 is biased at $-9700$ volts. Electrode 118 is electrically connected to photodiode 132 and is grounded. The bias voltages are supplied by suitable voltage sources (not shown).

The photodiode 132 is preferably an avalanche photodiode and is mounted on axis 122. The photodiode 132 is selected to produce electron multiplication when impacted by energetic electrons from photocathode 130. In a preferred embodiment, the photodiode 132 is a GaAs/AlGaAs avalanche photodiode. Other suitable photodiodes include PIN photodiodes, as shown in FIG. 2 and described above in connection with the FEB ion detector.

Figure 6:
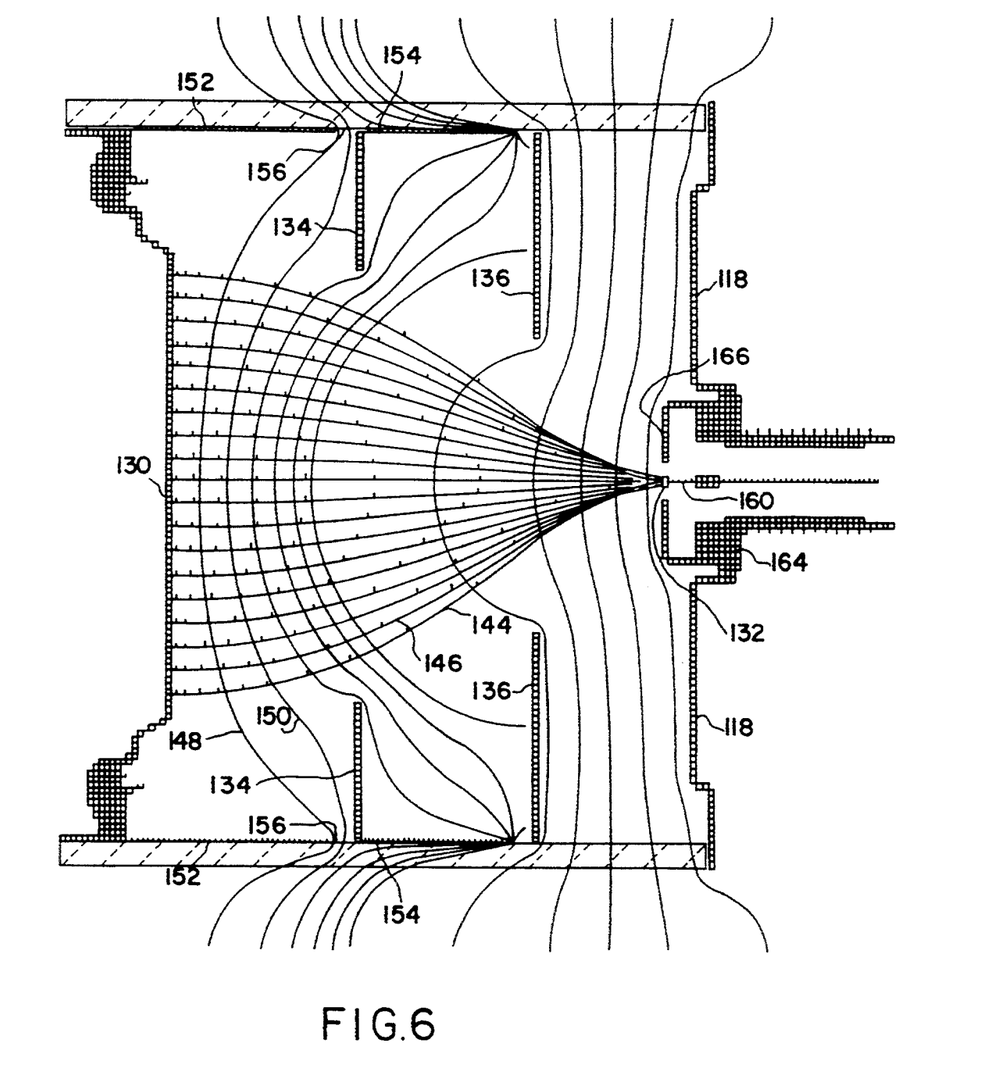
FIG. 6 is a schematic diagram of the photomultiplier tube of FIG. 5, illustrating the conductive portions of the tube and the resulting equipotential electric field lines and electron trajectories.

As noted above, electrical charges may build up on an inside surface 142 of sidewall 116. The sidewall 116 may, for example, be a ceramic material having a thickness on the order of about 0.065 inch. As shown in FIG. 6, electrons emitted from photocathode 130 are focused by electrodes 134 and 136 along trajectories 144, 146, etc. that are incident on photodiode 132. Equipotential lines 148, 150, etc. are established by the electrode configuration. When electrical charge builds up on the inside surface 142, the field configuration and, hence, the electron trajectories 144, 146 may be affected such that the electrons are no longer focused on photodiode 132.

To overcome this problem, a conductor is located on or adjacent to sidewall 116 of vacuum envelope 110. In the embodiment of FIG. 5, the conductor includes conductors 152 and 154 on an outside surface of sidewall 116. The conductor 152 is electrically connected to photocathode 130, and the conductor 154 is electrically connected to electrode 134. A gap 156 is provided between conductors 152 and 154 to prevent photocathode 130 from being short circuited to electrode 134. In the above example, the gap 156 can be relatively small, since the voltage difference between electrode 134 and photocathode 130 is on the order of 100 volts.

The effect of the conductors 152 and 154 is believed to be as follows. The charges on inside surface 142 of sidewall 116, believed to be positive electrical charges, are passivated by electrical charges of equal magnitude and opposite polarity on conductors 152 and 154. This causes electrical fields resulting from the charges on inside surface 142 to be confined to the regions between the inner and outer surfaces of sidewall 116. The charges on the inner and outer surfaces of sidewall 116 effectively form a capacitor, and minimal fringing electric fields extend from these charges into the vacuum region 112 between photocathode 130 and photodiode 132. As a result, the electrical charges on inside surface 142 do not appreciably affect the electron trajectories 144, 146, etc. followed by electrons between photocathode 130 and photodiode 132.

The conductors 152 and 154 can be implemented in any convenient manner such as metal foil or metallic coatings on the outside surface of sidewall 116. Both metal foil and conductive coatings on the outside surface of the photomultiplier tube have been found to result in stable tube operation. An advantage of a coating on the outside surface is that air voids between the sidewall 116 and the conductor are eliminated. Such voids may cause anisotropy in the electron optics within the photomultiplier tube. A preferred embodiment is to use a metallic paint, such as silver paint, to coat the outside surface of sidewall 116. Gap 156 between conductors 152 and 154 must be sufficiently wide to stand off the voltages applied to the respective electrodes. As best seen in FIG. 6, the gap 156 between conductors 152 and 154 is shielded, or shadowed, from a direct line of sight to photodiode 132 by electrode 134, thereby minimizing the possibility of charge build-up on the sidewall 116 in the region of gap 156.

It is noted that a conductor is not applied to the outside surface of sidewall 116 in a region 158, between electrode 136 and electrode 118. This portion of the sidewall 116 is preferably not provided with a metallic coating for several reasons. Most of the 10 kilovolts applied to the photomultiplier tube appears between electrodes 136 and 118. Thus, a relatively large insulating gap is required. Furthermore, it has been found that the electrons scattered from photodiode 132 follow trajectories toward the opposite end of the tube adjacent to photocathode 130. Finally, in the region near photodiode 132, the electrons are accelerated to relatively high velocities, and the electrical charges on sidewall 116 have a lesser effect on the electron trajectories.

As an alternative, conductors corresponding to conductors 152 and 154 can be located on inside surface 142 of sidewall 116. This is because it has been determined that good focusing of the electron trajectories 144, 146, etc. onto the photodiode 132 is possible and may be slightly improved using conductors 152 and 154. In this case, electrical charges which would otherwise build up on the insulating surface 142 are conducted away by the conductors thereon, thereby preventing charge build-up. This approach is effective in preventing charge build-up, but is less desirable than placing the conductors 152 and 154 on the outside surface of sidewall 116, since conductors within the vacuum envelope 110 may outgas and reduce the life of the photomultiplier tube.

The connector assembly 120 includes a center conductor 160, mounted in a ceramic insulator 162. The ceramic insulator 162 is supported by an outer conductor 164. The ceramic insulator 162 is brazed to the center conductor 160 and to the outer conductor 164. The outer conductor 164 is welded to electrode 118 to form a vacuum tight assembly. Photodiode 132 is mounted on the end of center conductor 160 that extends into vacuum region 112 so as to substantially cover the center conductor 160. The ceramic insulator 162 includes a metallization 166, shown in FIG. 6, which is electrically connected to electrode 118, and which surrounds but does not contact the center conductor 160. A thin wire 168 is connected between metallization 166 and the top contact pad of photodiode 132. The connector assembly 120 further includes a conventional SMA-type coaxial connector 170 secured to center conductor 160 and outer conductor 164 by a lock nut 172.

The connector assembly 120 has several advantages in the operation of the hybrid photomultiplier tube. The connector functions as a portion of the vacuum envelope 110 and thus affects the shape of the electric fields within the tube. The internal surface of the connector is exposed to the open volume of the tube so that the surface can be electron scrubbed during tube processing, resulting in a cleaner tube. The connector supports the photodiode 132 on center conductor 160 which is completely covered by the photodiode 132. Thus, the bias voltage applied to the photodiode 132 does not affect the electric fields which focus electrons onto the photodiode. The preferred photodiode 132 has a relatively low operating voltage, thus permitting use of an industry-standard SMA output connector. The connector is impedance matched to 50 ohms to permit a flat frequency response well beyond 1 GHz.

Figure 7:
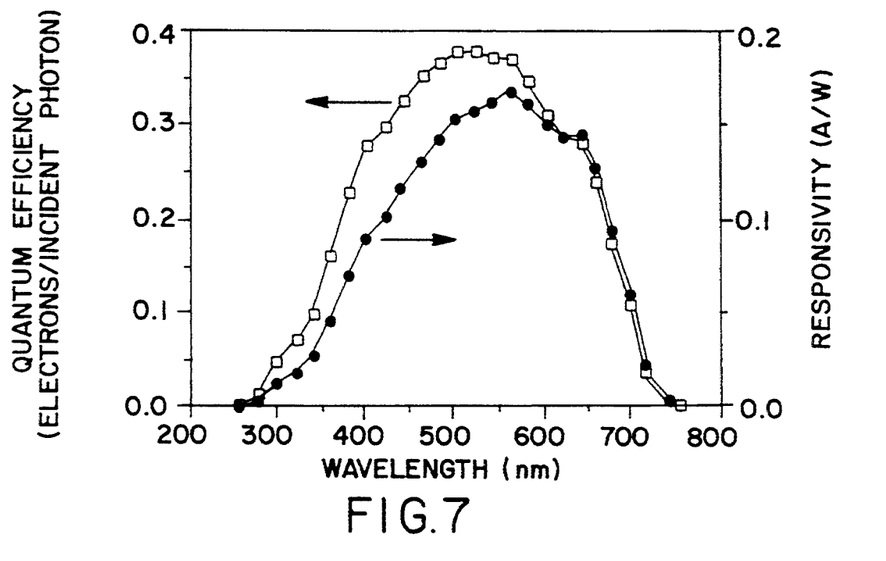
FIG. 7 is a graph of quantum efficiency and responsivity as a function of wavelength for a gallium arsenide phosphide photocathode.
Figure 8:
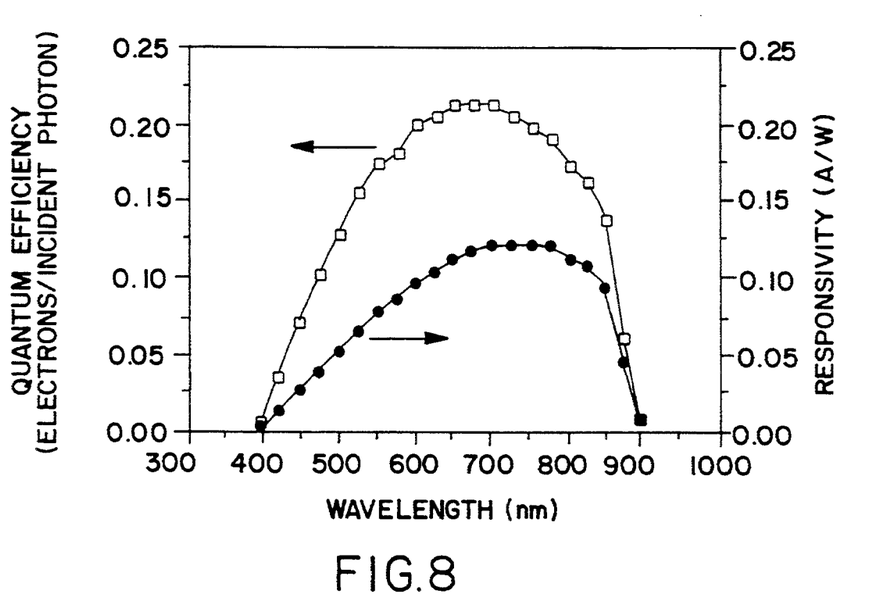
FIG. 8 is a graph of quantum efficiency and responsivity as a function of wavelength for a gallium arsenide photocathode.
Figure 9:
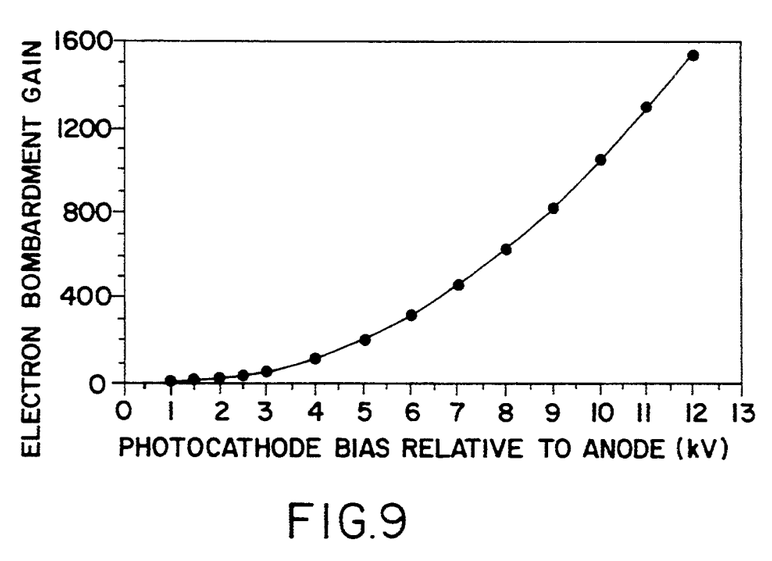
FIG. 9 is a graph of electron bombardment gain as a function of photocathode bias relative to the anode.

In a preferred embodiment, the photocathode 130 has a diameter of 24.5 mm and the window 114 is fabricated of Corning type 7056 glass. The vacuum envelope 110 has a diameter of 1.6 inches and a length of 2.0 inches. The quantum efficiency and responsivity for a gallium arsenide phosphide photocathode, as described in the aforementioned article by J. P. Edgecumbe et al, are plotted as a function of wavelength in FIG. 7. The quantum efficiency and responsivity for a gallium arsenide photocathode, as described in the aforementioned article by K. A. Costello et al, are plotted as a function of wavelength in FIG. 8. In both cases, the gain is expected to be greater than 20,000 and the risetime to be less than 0.5 nanosecond. The electron bombardment gain is plotted as a function of photocathode bias relative to the anode in FIG. 9.

The use of a conductor adjacent to or on the vacuum envelope to limit the effect of electrical charges on the envelope wall on electron trajectories has been described thus far in connection with a hybrid photomultiplier tube. It is expected that this technique, i.e., passivation of charge build-up by a conductor on the outside surface of the vacuum envelope, can be utilized in any photomultiplier tube and, more generally, in any vacuum tube which includes a vacuum envelope, a charged particle source and optics for controlling the trajectories of the charged particles within the vacuum envelope. Furthermore, the conductor can be used on the FEB ion detector described above. By limiting the electric fields resulting from the charges to the region within the wall of the vacuum envelope, the effect of the charges on charged particle trajectories is minimized. As noted above, the conductor can be placed on or adjacent to the vacuum envelope wall in any region where it is desired to limit the effects of charges on the inside surface of the vacuum envelope.

While there have been shown and described what are at present considered the preferred embodiments of the invention, it will be obvious to those skilled in the art that various changes and modifications may be made therein without departing from the scope of the invention as defined by The appended claims.

What is claimed is:

1. A photomultiplier tube comprising:
   a photocathode for emitting electrons in response to incident photons;
   a detector for collecting and multiplying said electrons emitted by said photocathode and providing an output signal representative of said incident photons;
   one or more electrodes for focusing said electrons on said detector;
   means for accelerating said electrons toward said detector;
   a vacuum envelope defining a vacuum region between said photocathode and said detector, said vacuum envelope including a sidewall adjacent to a path of said electrons between said photocathode and said detector; and
   a conductor disposed on or adjacent to said sidewall for reducing the effect of electrical charges on said sidewall on trajectories of said electrons.

2. A photomultiplier tube as defined in claim 1 wherein said conductor is disposed on an outside surface of said sidewall.

3. A photomultiplier tube as defined in claim 2 wherein said conductor comprises a conductive coating on said outside surface.

4. A photomultiplier tube as defined in claim 3 wherein said conductive coating comprises silver.

5. A photomultiplier tube as defined in claim 2 wherein said conductor includes a first portion electrically connected to said photocathode and a second portion electrically connected to one of said electrodes, said first and second portions being spaced apart by a gap.

6. A photomultiplier tube as defined in claim 1 wherein said vacuum envelope includes a window and said photocathode is located on an inside surface of said window.

7. A photomultiplier tube as defined in claim 6 wherein said photocathode comprises a group III-V semiconductor material.

8. A photomultiplier tube as defined in claim 6 wherein said photocathode is selected from a group consisting of GaAs, GaAsP, InP and InP/InGaAs.

9. A photomultiplier tube as defined in claim 1 wherein said electrodes include first and second spaced-apart electrodes having apertures for passing said electrons.

10. A photomultiplier tube as defined in claim 1 wherein said detector comprises an avalanche photodiode.

11. A photomultiplier tube as defined in claim 10 wherein said vacuum envelope includes a coaxial feedthrough connected to said photodiode, said coaxial feedthrough coupling said output signal externally of said vacuum envelope.

12. A photomultiplier tube as defined in claim 11 wherein said coaxial feedthrough includes a center conductor and wherein said photodiode is mounted on said center conductor.

13. A photomultiplier tube as defined in claim 12 wherein said photodiode covers an end of said center conductor.

14. In a vacuum tube of the type including a vacuum envelope, a charged particle source within said vacuum envelope for emitting charged particles, a photodiode within said vacuum envelope for detecting said charged particles and optics for controlling the trajectories of said charged particles within said vacuum envelope, the improvement comprising:
   a conductor disposed on or adjacent to said vacuum envelope for reducing the effect of electrical charges on said vacuum envelope on the trajectories of said charged particles.

15. An improved vacuum tube as defined in claim 14 wherein said charged particle source comprises an electron source.

16. An improved vacuum tube as defined in claim 15 wherein said conductor is disposed on an outside surface of said vacuum envelope.

17. An improved vacuum tube as defined in claim 16 wherein said conductor comprises a coating on said outside surface.

18. An improved vacuum tube as defined in claim 14 wherein said vacuum tube comprises a photomultiplier tube.

19. A photomultiplier tube comprising:
   a photocathode for emitting electrons in response to incident photons;
   a photodiode for collecting and multiplying said electrons and providing an output signal representative of said incident photons;
   electron optical means for controlling the trajectories of said electrons between said photocathode and said photodiode;
   means for applying an electric field between said photocathode and said photodiode for accelerating said electrons between said photocathode and said photodiode;
   a vacuum envelope defining a vacuum region between said photocathode and said photodiode; and
   a conductor disposed on at least a portion of an outside surface of said vacuum envelope for reducing the effect of electrical charges on said vacuum envelope on the trajectories of said electrons.

20. A photomultiplier tube as defined in claim 19 wherein said electron optical means comprises first and second focusing electrodes.

21. A photomultiplier tube as defined in claim 20 wherein said conductor comprises a first conductive coating formed on said vacuum envelope and electrically connected to said photocathode and a second conductive coating formed on said vacuum envelope and electrically connected to said first focusing electrode, said first and second conductive coatings being spaced apart by a gap.

22. A photomultiplier tube as defined in claim 21 wherein said gap between said first and second conductive coatings is located on a part of said vacuum envelope that is blocked by said electron optical means from a direct line of sight to said photodiode.

23. A photomultiplier tube as defined in claim 19 wherein said vacuum envelope includes a window and said photocathode is located on an inside surface of said window.

24. A photomultiplier tube as defined in claim 23 wherein said photocathode comprises a group III-V semiconductor material.

25. A photomultiplier tube as defined in claim 19 wherein said vacuum envelope includes a coaxial feedthrough for coupling said output signal externally of said vacuum envelope and wherein said photodiode is mounted on a center conductor of said coaxial feedthrough.

26. A photomultiplier tube comprising:
a photocathode for emitting electrons in response to incident photons;
a detector for collecting and multiplying said electrons emitted by said photocathode and providing an output signal representative of said incident photons;
electron optical means for controlling the trajectories of said electrons between said photocathode and said detector;
means for accelerating said electrons toward said detector;
a vacuum envelope defining a vacuum region between said photocathode and said detector; and
a conductor disposed on at least a portion of an inside surface of said vacuum envelope for reducing the effect of electrical charges on said vacuum envelope on the trajectories of said electrons.

* * * * *